United States Patent [19]

Alt

[11] 4,345,938
[45] Aug. 24, 1982

[54] HERBICIDAL 2-HALOACETANILIDES

[75] Inventor: Gerhard H. Alt, University City, Mo.

[73] Assignee: Monsanto Company, St. Louis, Mo.

[21] Appl. No.: 133,764

[22] Filed: Mar. 25, 1980

[51] Int. Cl.$^3$ .................... A01N 37/22; C07C 103/32
[52] U.S. Cl. ........................................ 71/118; 564/214
[58] Field of Search .................. 260/562 B; 71/118; 564/214

[56] References Cited

U.S. PATENT DOCUMENTS

| | | | |
|---|---|---|---|
| 3,268,584 | 8/1966 | Olin | 260/562 B |
| 3,442,945 | 5/1969 | Olin | 260/562 |
| 3,663,200 | 5/1972 | Olin | 71/118 |
| 3,773,498 | 11/1973 | Fischer | 71/92 |
| 3,955,959 | 5/1976 | Skipper | 71/118 |
| 4,152,137 | 5/1979 | Martin | 71/118 X |
| 4,168,965 | 9/1979 | Vogel et al. | 71/118 |

*Primary Examiner*—Catherine L. Mills
*Attorney, Agent, or Firm*—William I. Andress; Howard C. Stanley

[57] ABSTRACT

The disclosure herein relates to a group of N-alkyl-2-haloacetanilide compounds, herbicidal compositions containing said compounds as the active ingredient and herbicidal method of use in various crops, particularly transplant rice. The herbicides herein are particularly effective against annual and perennial weeds commonly associated with rice.

12 Claims, No Drawings

HERBICIDAL 2-HALOACETANILIDES

BACKGROUND OF THE INVENTION

1. Field of the Invention

This invention pertains to the field of 2-haloacetanilides and their use in the agronomic arts, e.g., as herbicides, particularly for use in transplant rice.

2. Description of the Prior Art

The invention compounds are characterized as 2-chloroacetanilides having an n-butoxy radical in one ortho position, an ethyl radical in the other position, and as a substituent on the anilide nitrogen ring a $C_{1-5}$ alkyl radical, perferably methyl or ethyl.

The prior art relevant to this invention includes numerous disclosures of 2-haloacetanilides which may be unsubstituted or substituted with a wide variety of substituents on the anilide nitrogen atom and/or on the anilide ring including alkyl, alkenyl, alkynyl, alkoxy, polyalkoxy, alkoxyalkyl, heterocyclyl, halogen, etc., radicals. The most relevant compounds of the prior art in this area appear to be those disclosed in the following references: U.S. Pat. Nos. 3,268,584, 3,442,945, 3,773,492 and 4,152,137. However, none of those prior art references disclose any data for compounds of the type disclosed herein as being useful transplant rice herbicides, nor do they disclose or suggest the particular species of this invention.

The 2-haloacetanilides of the prior art which are known to have utility as transplant rice herbicides differ significantly in structure from those disclosed herein. Specifically, said prior art herbicides all contain lower alkyl radicals in both ortho positions to the anilide nitrogen atom and an alkoxyalkyl radical on said nitrogen atom. Accordingly, those prior art rice herbicides are non-related and non-suggestive of those disclosed herein. However, in order to provide a basis for comparison, the relative herbicidal efficacy of preferred compound of this invention is compared with that of relevant prior art herbicides; data are presented in tables herein.

The above-mentioned 2-haloacetanilides of the prior art are MACHETE ® (registered trademark of Monsanto Company), the active ingredient of which is 2',6'-diethyl-N-(n-butoxymethyl)-2-chloroacetanilide (common name "butachlor"); 2',6'-diethyl-N-(n-butoxyethyl)-2-chloroacetanilide ("ethyl butachlor" herein); 2-tert-butyl-6-methyl-N-(n-butoxymethyl)-2-chloroacetanilide (common name "terbuchlor"), and 2',6'-diethyl-N-(2-propoxyethyl)-2-chloroacetanilide (common name "pretalachlor"). Butachlor and ethyl butachlor are disclosed as rice herbicides in U.S. Pat. No. 3,663,200; terbuchlor is disclosed as a transplant rice herbicide in U.S. Pat. No. 3,955,959 and pretalachlor is disclosed as a rice herbicide in U.S. Pat. No. 4,168,965. Of the foregoing herbicides, only MACHETE herbicide has achieved commercial status.

While the above rice herbicides have been found useful, there is a continuing need for improved rice herbicides which control resistant weeds of economical significance at lower rates of application, maintain control or suppression of such weeds for longer periods of time, while maintaining safety to the rice crop and improved toxicity with respect to fish and mammals.

The above prior art herbicides have been found to share one or more undesirable properties as transplant rice herbicides. Among certain disadvantages of those prior art herbicides are: (1) their generally weak performance in the control and/or suppression of the economically-significant resistant perennial weeds Eleocharis kuroguwai and *Sagittaria trifolia* and (2) diminishing efficacy in the control or suppression of the perennial weed *Cyperus serotinus* and the annual weeds *Echinochloa crus-galli* and, to a lesser extent, *Monochoria vaginalis*, within a period from 2–6 weeks.

These performance weaknesses are particularly apparent at lower rates of application, i.e. down to 0.17 lb/A (0.19 kg/ha) and lower. In fact, field tests have shown that in some treatments some of the prior art herbicides failed to selectively control Eleocharis kuroguwai at rates below 2.67 lb/A (3 kg/ha) or even up to 5.36 lb/A (6 kg/ha), or higher, for periods as short as 2 or 3 weeks. Similarly, in field tests, it was also found that some of the above prior art rice herbicides failed to provide any meaningful suppression of Sagittaria trifolia after four or five weeks.

It is, therefore, an object of this invention to provide a class of herbicides which are particularly useful in transplant rice.

A further object of this invention is the provision of selected herbicides which: (1) are safe (i.e., produce no more than about 15% injury) on transplant rice at rates up to at least 5.0 lb/A (5.60 kg/ha); (2) selectively control *Echinochloa crus-galli, Monochoria vaginalis* and *Cyperus serotinus* at rates below 0.35 kg/ha (0.34 lb/A) for up to at least seven weeks; (3) selectively control Eleocharis kuroguwai at rates as low as 3.0 kg/ha (2.67 lb/A) for as long as five weeks and (4) provide increased suppression of Sagittari trifolia for up to seven weeks.

It is a further object of this invention to provide a transplant rice herbicide having improved fish toxicity relative to the above prior art herbicides.

Finally, it is an advantage of the herbicides of this invention that they are safe and require no special handling procedures.

The above and other objects of the invention will become more apparent from the detailed description below.

SUMMARY OF THE INVENTION

The present invention relates to herbicidally active compounds, herbicidal compositions containing these compounds as active ingredients and herbicidal method of use of said compositions in various crops, particularly transplant rice.

It has now been found that a selective group of 2-haloacetanilides characterized by specific combinations of radicals on the anilide nitrogen atom, a specific alkoxy radical in one ortho position and an ethyl radical in the other ortho position possess unexpectedly superior and outstanding selective herbicidal properties as transplant rice herbicides vis-a-vis prior art herbicides of related structure of the most relevant prior art, including a commercial rice herbicide.

A primary feature of the herbicidal compositions of this invention is their ability to control and/or suppress annual and perennial weeds in transplant rice, particularly the prevalent and economically-significant annuals such as Echinochloa crus-galli, Monochoria vaginalis and resistant perennial species such as *Cyperus serotinus, Eleocharis kuroguwai* and *Sagittaria trifolia* and other noxious weeds.

The compounds of this invention are characterized by the formula

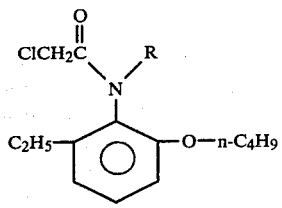

wherein R is a $C_{1-5}$ alkyl radical, including the n-, sec- and iso-propyls, butyls and pentyls, but preferably methyl or ethyl.

The preferred species of compounds of this invention are:
N-methyl-2'-n-butoxy-6'-ethyl-2-chloroacetanilide and
N-ethyl-2'-n-butoxy-6'-ethyl-2-chloroacetanilide The utility of the compounds of this invention as the active ingredient in herbicidal compositions formulated therewith and the method of use thereof will be described below.

DETAILED DESCRIPTION OF THE INVENTION

The compounds of this invention may be made in a variety of ways. For example, these compounds may be prepared by a process involving the N-alkylation of the anion of the appropriate secondary 2-haloacetanilide with an alkylating agent under basic conditions. The N-alkylation process is the invention of others and is described in more detail in co-pending U.S. Ser. No. 63,005 filed Aug. 2, 1979, assigned to the same assignee herein and in Examples 1 and 2 herein.

EXAMPLE 1

This example describes the preparation of one preferred species, N-methyl-2'-n-butoxy-6'-ethyl-2-chloroacetanilide. In this example dimethyl sulfate is used as the alkylating agent to prepare the N-methyl-2-chloroacetanilide from the corresponding sec-amide anion.

To a chilled (15° C.) mixture of 2'-n-butoxy-6'-ethyl-2-chloroacetanilide, 6.2 g (0.023 mol), dimethyl sulfate, 3.0 g (0.024 mol), and 2.3 g of triethyl benzyl ammonium chloride in 250 ml of methylene chloride, was added all at once 55 ml of 50% NaOH and the mixture was stirred for 15.0 minutes. Water (100 ml) was added, and the resulting layers separated; the organic layer was washed with water, dried with $MgSO_4$, then evaporated by Kugelrohr to give 5.8 g (89% yield) of a clear liquid, b.p. 115° C. at 0.05 mm Hg.

Anal. Calc'd for $C_{15}H_{22}ClNO_2$ (%): C, 63.48; H. 7.81; Cl, 12.49 Found: C, 63.52; H, 7.83; Cl, 12.52
The product was identified as N-methyl-2'-n-butoxy-6'-ethyl-2-chloroacetanilide.

EXAMPLE 2

2'-n-butoxy-6'-ethyl-2-chloroacetanilide, 5.4 gms (0.02 mol), diethyl sulfate, 3.4 gms (0.22 mol) and 2.0 gms of triethyl benzyl ammonium chloride were mixed in 150 ml of $CH_2Cl_2$ under cooling. Forty-five (45) ml of 50% NaOH were then added all at once at 18° C. and the mixture stirred for ten minutes. Water (150 ml) was added and the resultant layers separated. The organic layer was washed with water, dried over $MgSO_4$ and evaporated by Kugelrohr. A clear liquid (yellows), b.p. 113° C. at 0.05 mm Hg was obtained in 22% yield (1.3 gms).

Anal. Calc'd for $C_{16}H_{24}ClNO_2$ (%): C, 64.53; H, 8.12; Cl, 11,90. Found: C, 64.26; H, 8.16; Cl, 11.79
The product was identified as N-ethyl-2'-n-butoxy-6'-ethyl-2-chloroacetanilide.

The secondary anilides used as starting materials in the above N-alkylation process are prepared by known methods, e.g., haloacetylation of the corresponding aniline. For example, the starting sec-anilide used in Examples 1 and 2 was prepared by mixing 2-n-butoxy-6-ethylaniline in methylene chloride and stirring vigorously with a 10% sodium hydroxide solution while a solution of chloroacetyl chloride in methylene chloride was added over a period of about one-half hour, keeping the temperature between 15°–25° C. with external cooling. The reaction mixture was stirred for about a further 60 minutes. After the addition was complete, the layers separated and the methylene chloride layer washed with water, dried and evaporated in vacuo to obtain a white solid, m.p. 132° C.

Anal. Calc'd for $C_{14}H_{20}ClNO_2$ (%): C, 62.33; H, 7.47; Cl, 13.14. Found: C, 62.33; H, 7.49; Cl, 13.16
The product was identified as 2'-n-butoxy-6'-ethyl-2-chloroacetanilide.

The primary amine used to prepare the above-mentioned secondary anilide may be prepared by known means, e.g., by catalytic reduction of the corresponding 2-alkoxy-6-alkyl-nitrobenzene in ethanol using platinum oxide catalyst.

As noted above, the compounds of this invention have been found to be effective against major Asian weeds as transplant rice herbicides. However, pre-emergence and post-emergence herbicidal activity against other weeds in other crops has also been shown. Tables I and II summarize results of tests conducted to determine the pre-emergent herbicidal activity of the compounds of this invention.

The pre-emergent tests were conducted as follows:
A good grade of top soil is placed in aluminum pans and compacted to a depth of three-eights to one-half inch from the top of the pan. On the top of the soil is placed a number of seeds or vegetative propagules of various plant species. The soil required to level fill the pans after seeding or adding vegetative propagules is weighted into a pan. The soil and a known amount of the active ingredient applied in a solvent or as a wettable powder suspension are thoroughly mixed, and used to cover the prepared pans. After treatment, the pans are moved into a greenhouse bench where they are watered by subirrigation as needed to give adequate moisture for germination and growth.

Approximately 2 weeks after seeding and treating, the plants were observed and the results recorded. Tables I and II below summarize such results. The herbicidal rating was obtained by means of a fixed scale based on the percent injury of each plant species. The ratings are defined as follows:

| % Control | Rating |
---|---
| 0–24 | 0 |
| 25–49 | 1 |
| 50–74 | 2 |
| 75–100 | 3 |
| Undetermined | 5 |

The plant species utilized in one set of tests, the data for which are shown in Table I, are identified by letter in accordance with the following legend:

| A | Canada Thistle | E | Lambsquarters | I | Johnsongrass |
|---|---|---|---|---|---|
| B | Cocklebur | F | Smartweed | J | Downey Brome |
| C | Velvetleaf | G | Yellow Nutsedge | K | Barnyardgrass |
| D | Morningglory | H | Quackgrass | | |

TABLE I

| Compound of Example No. | kg/h | Pre-Emergent Plant Species | | | | | | | | | | |
|---|---|---|---|---|---|---|---|---|---|---|---|---|
| | | A | B | C | D | E | F | G | H | I | J | K |
| 1 | 11.2 | 3 | 5 | 2 | 1 | 3 | 3 | 3 | 3 | 3 | 3 | 3 |
|   | 5.6  | 3 | 5 | 2 | 2 | 3 | 2 | 3 | 3 | 3 | 3 | 3 |
| 2 | 11.2 | 5 | 0 | 1 | 2 | 3 | 3 | 3 | 3 | 3 | 3 | 3 |
|   | 5.6  | 5 | 0 | 0 | 0 | 3 | 3 | 3 | 3 | 2 | 3 | 3 |

The compounds were further tested by utilizing the above procedure on the following plant species:

| L | Soybean | R | Hemp Sesbania |
|---|---|---|---|
| M | Sugarbeet | E | Lambsquarters |
| N | Wheat | F | Smartweed |
| O | Rice | C | Velvetleaf |
| P | Sorghum | J | Downy Brome |
| B | Cocklebur | S | Panicum Spp. |
| Q | Wild Buckwheat | K | Barnyardgrass |
| D | Morningglory | T | Crabgrass |

The results are summarized in Table II.

TABLE II

| Compound of Example No. | kg/h | Pre-Emergent Plant Species | | | | | | | | | | | | | | |
|---|---|---|---|---|---|---|---|---|---|---|---|---|---|---|---|---|
| | | L | M | N | O | P | B | Q | D | R | E | F | C | J | S | K | T |
| 1 | 5.6   | 1 | 3 | 3 | 3 | 3 | 0 | 3 | 3 | 3 | 3 | 3 | 1 | 3 | 3 | 3 | 3 |
|   | 1.12  | 0 | 2 | 2 | 3 | 3 | 5 | 2 | 2 | 3 | 3 | 3 | 1 | 3 | 3 | 3 | 3 |
|   | 0.28  | 0 | 1 | 2 | 3 | 3 | 5 | 1 | 0 | 3 | 2 | 2 | 0 | 3 | 3 | 3 | 3 |
|   | 0.06  | 0 | 0 | 1 | 1 | 2 | 0 | 1 | 0 | 3 | 0 | 0 | 0 | 3 | 3 | 3 | 3 |
|   | 0.01  | 0 | 0 | 0 | 1 | 0 | 5 | 1 | 5 | 2 | 0 | 0 | 0 | 1 | 1 | 2 | 3 |
|   | 0.006 | 0 | 0 | 0 | 1 | 0 | 5 | 0 | 0 | 2 | 0 | 0 | 0 | 0 | 0 | 1 | 1 |
| 2 | 5.6   | 1 | 2 | 3 | 3 | 3 | 1 | 2 | 1 | 2 | 3 | 3 | 1 | 3 | 3 | 3 | 5 |
|   | 1.12  | 0 | 2 | 2 | 3 | 3 | 0 | 1 | 0 | 2 | 2 | 2 | 0 | 3 | 3 | 3 | 5 |
|   | 0.28  | 0 | 1 | 1 | 1 | 1 | 0 | 0 | 0 | 0 | 0 | 0 | 3 | 3 | 3 | 5 |   |
|   | 0.06  | 0 | 0 | 0 | 0 | 0 | 0 | 0 | 0 | 0 | 0 | 0 | 0 | 1 | 1 | 3 | 5 |
|   | 0.01  | 0 | 0 | 0 | 0 | 0 | 0 | 0 | 0 | 0 | 0 | 0 | 0 | 0 | 0 | 1 | 5 |

The herbicides of this invention have been found to possess unexpectedly superior properties as transplant rice herbicides, most particularly in the effective control and/or suppression of the economically significant annual weeds, *Echinochloa crus-galli* and *Monochoria vaginalis* and the resistant perennials *Cyperus serotinus, Eleocharis Kuroguwai* and *Sagittaria trifolia*, while also controlling or suppressing many other less-resistant perennial and annual weeds.

In order to illustrate the unexpectedly superior properties of compounds according to this invention both on an absolute basis and on a relative basis, comparative tests were conducted in the greenhouse and in the field. In some of these tests, known transplant rice herbicides (including MACHETE herbicide, the only current commercial 2-haloacetanilide rice herbicide) were tested for comparative purposes. The prior art 2-haloacetanilide herbicides are identified as follows:

A. 2',6'-diethyl-N-(n-butoxymethyl)-2-chloroacetanilide (U.S. Pat. No. 3,663,200).
B. 2',6'-diethyl-N-(n-butoxyethyl)-2-chloroacetanilide (U.S. Pat. No. 3,663,200).
C. 2'-methyl-6'-tert-butyl-N-(n-butoxymethyl)-2-chloroacetanilide (U.S. Pat. No. 3,955,959).
D. 2',6'-diethyl-N-(n-propoxyethyl)-2-chloroacetanilide (U.S. Pat. No. 4,168,965).

In the discussion of data below, occasional reference is made to herbicide application rates symbolized as "$GR_{15}$" and "$GR_{85}$"; these rates are given in kilograms per hectare (kg/ha) which are convertible into pounds per acre (lbs/A) by dividing the kg/ha rate by 1.12. $GR_{15}$ defines the maximum rate of herbicide required to produce 15% or less crop injury, and $GR_{85}$ defines the minimum rate required to achieve 85% inhibition of weeds. The $GR_{15}$ and $GR_{85}$ rates are used as a measure of potential commercial performance, it being understood, of course, that suitable commercial herbicides may exhibit greater or lesser plant injuries within reasonable limits.

A further guide to the effectiveness of a chemical as a selective herbicide is the "selectivity factor" ("SF") for a herbicide in given crops and weeds. The selectivity factor is a measure of the relative degree of crop safety and weed injury and is expressed in terms of the $GR_{15}/GR_{85}$ ratio, i.e., the $GR_{15}$ rate for the crop divided by the $GR_{85}$ rate for the weed, both rates in kg/ha (lb/A.)

Since crop tolerance and weed control are interrelated, a brief discussion of this relationship in terms of selectivity factors is meaningful. In general, it is desirable that crop safety factors, i.e., herbicide tolerance vlaues, be high, since higher concentrations of herbicide are frequently desired for one reason or another. Conversely, it is desirable that weed control rates be small, i.e., the herbicide possesses high unit activity, for economical and possibly ecological reasons. However, small rates of application of herbicide may not be adequate to control certain weeds and a larger rate may be required. Hence the best herbicides are those which control the greatest number of weeds with the least amount of herbicide and provide the greatest degree of crop safety, i.e., crop tolerance. Accordingly, use is made of selectivity factors (defined above) to quantify the relationship between crop safety and weed control; the higher the numerical value, the greater selectivity of the herbicide for weed control in a given crop.

In one comparative test in the greenhouse, herbicidal activity data were obtained and are presented in Table III comparing the relative efficacy of the compounds of Examples 1 and 2, representative compounds of this invention, with compound A (a commercial rice herbicide), as selective herbicides against economically-significant Asian weeds commonly associated with transplant rice.

The test procedure used in this greenhouse test is as follows: Ray silt loam top soil containing about 0.05% by weight of krillium and sifted through a 0.5 in. (0.6 cm) screen is fumigated about 5-10 days prior to use. Pots are then filled with said Ray silt loam soil to a level to allow for a 1 in. (2.54 cm) flooding depth. Rice plants (Bluebelle) of 2 to 3 weeks age are transplanted to the pots and bulbs or seeds of the test weeds also planted in the pots. The pots are then flooded and the test chemical applied to the surface of the flood water. The flood water is reduced to allow for germination of the Echinochloa crus-galli (barnyardgrass) seed and subsequently reflooded and maintained in that condition. Observations of percent inhibition using a scale of 0-100% are made about 3 weeks after transplant (WAT).

The test data in Table III for all compounds was obtained under identical test conditions. The weeds used in the tests herein have the following abbreviations in the tables: Echinochloa crus-galli (EC), *Monochloria vaginalis* (MV), *Cyperus Serotinus* (CS), *Eleocharis Kuroguwai* (EK) and *Sagittaria trifolia* (ST).

TABLE III

| Compound | Rate (Kg/Ha) | Percent Inhibition |  |  |  |  |  |
|---|---|---|---|---|---|---|---|
| | | Rice | EC | MV | CS | EK | ST |
| A | 2.24 | 15 | 100 | 100 | 100 | 100 | 15 |
| | 1.12 | 10 | 100 | 100 | 90 | 100 | 30 |
| | 0.56 | 10 | 100 | 100 | 85 | 100 | 45 |
| | 0.28 | 5 | 96 | 98 | 100 | 50 | 15 |
| Ex. 1 | 2.24 | 20 | 100 | 100 | 100 | 100 | 90 |
| | 1.12 | 15 | 100 | 100 | 100 | 100 | 85 |
| | 0.56 | 0 | 100 | 100 | 100 | 100 | 85 |
| | 0.28 | 5 | 100 | 100 | 85 | 100 | 75 |
| Ex. 2 | 2.24 | 25 | 100 | 100 | 100 | 100 | 55 |
| | 1.12 | 15 | 100 | 100 | 100 | 100 | 70 |
| | 0.56 | 10 | 100 | 100 | 100 | 100 | 25 |
| | 0.28 | 0 | 100 | 100 | 100 | 100 | 30 |

Reference to the data in Table III will show that in this sheet, both invention compounds exhibited higher unit activity (i.e. phytotoxicity per unit of herbicide applied) against every weed in the test than did Compound A. In more particular, at 0.28 kg/ha (0.25 lb/A) the compound of Example 2 gave 100% control of every weed, except ST; the compound of Example 1 gave 100% control of three of five weeds, i.e., EC, MV and EK, at 0.28 kg/ha, and all weeds, except ST, at 0.56 kg/ha (0.5 lb/A). But for the slightly anomalous value in CS, Compound A did not give 100% control of any weed in the test, at 0.28 kg/ha although control of EC, MV and EK were complete at 0.56 kg/ha. A most significant fact of the test data in Table III is the relative control of the perennial weeds, EK, at 0.28 kg/ha, and ST, at all test rates, of the invention compounds vis-a-vis Compound A. But for the slightly anomalous value of 45% control of ST at 0.56 kg/ha, the invention compounds exhibited substantially greater control of ST than Compound A, by a factor of at least two. The outstanding superior control of ST by the compound of Example 1 vs. that of Compound A at all rates of application is particularly striking. It will also be noted that in this test, the compound of Example 1 exhibited positive selective control of ST in rice at 0.56 kg/ha, whereas greatly improved suppression of that weed was realized by the compound of Example 2 vs. Compound A. The data in Table III also indicate that rice was slightly more tolerant of Compound A than the invention compounds at 2.24 kg/ha, though not greatly so.

In further comparative tests, a preferred compound of this invention (Example 1) was tested in the field with prior art Compounds A-D. These tests were conducted under conditions reflecting herbicide application times generally favorable to all herbicides in the test. The timing of application of herbicides to transplant rice is very important, whether, as in some instances, prior to transplanting the rice; in other instances, at the time of transplanting or else after transplanting. Application times are conventionally referred to as "days before transplant" (DBT) or "days after transplant" ("DAT"). The field test data in Table IV was obtained from a test in which the herbicides were applied at the time of transplant, i.e., "0 DAT", with observations being made weekly up to six weeks after transplant ("WAT") beginning at two weeks after transplant; for illustrative and representative purposes, only the early, middle and late period observations, i.e., 2 WAT, 4 WAT and 6 WAT, are shown in Table IV. The data in Table IV is for rates of application common to all herbicides in the test, i.e., from 3.0 kg/ha (2.67 lb/A) down to 0.375 kg/ha (0.34 lb/A). All herbicides were applied at their actual or expected use rates, i.e., as granules containing 2.5% by weight herbicide for the compound of Example 1, Compounds B, C and D and 5.0% by weight for Compound A.

TABLE IV

| | | Percent Inhibition (Herbicide Applied 0 DAT) | | | | | | | | | | | | | | | | | |
|---|---|---|---|---|---|---|---|---|---|---|---|---|---|---|---|---|---|---|---|
| | | Rice WAT | | | EC WAT | | | MV WAT | | | CS WAT | | | EK WAT | | | ST WAT | | |
| Compound | Rate (Kg/Ha) | 2 | 4 | 6 | 2 | 4 | 6 | 2 | 4 | 6 | 2 | 4 | 6 | 2 | 4 | 6 | 2 | 4 | 6 |
| Ex. 1 | 3.0 | 25 | 22 | 23 | 98 | 100 | 100 | 100 | 100 | 100 | 95 | 99 | 100 | 97 | 92 | 65 | 47 | 22 | 18 |
| | 1.5 | 5 | 0 | 2 | 100 | 100 | 100 | 100 | 100 | 100 | 92 | 83 | 73 | 87 | 83 | 37 | 30 | 8 | 5 |
| | 0.75 | 3 | 0 | 2 | 98 | 100 | 98 | 100 | 99 | 97 | 62 | 53 | 25 | 82 | 75 | 50 | 43 | 12 | 8 |
| | 0.375 | 10 | 7 | 5 | 97 | 100 | 100 | 98 | 100 | 93 | 77 | 73 | 50 | 73 | 40 | 3 | 42 | 8 | 5 |
| A | 3.0 | 10 | 2 | 3 | 98 | 100 | 100 | 100 | 100 | 100 | 73 | 68 | 50 | 90 | 88 | 68 | 42 | 33 | 12 |
| | 1.5 | 8 | 23 | 5 | 95 | 100 | 97 | 100 | 100 | 100 | 90 | 82 | 77 | 83 | 78 | 28 | 60 | 33 | 20 |
| | 0.75 | 2 | 0 | 0 | 90 | 100 | 100 | 100 | 98 | 100 | 95 | 93 | 93 | 45 | 22 | 0 | 52 | 20 | 15 |
| | 0.375 | 8 | 10 | 7 | 60 | 72 | 60 | 98 | 87 | 82 | 67 | 67 | 63 | 65 | 33 | 10 | 37 | 22 | 7 |
| B | 3.0 | 7 | 2 | 3 | 97 | 100 | 100 | 100 | 100 | 97 | 72 | 62 | 37 | 100 | 94 | 72 | 32 | 30 | 13 |
| | 1.5 | 10 | 3 | 0 | 90 | 98 | 98 | 98 | 100 | 100 | 82 | 83 | 45 | 73 | 65 | 17 | 62 | 12 | 7 |
| | 0.75 | 3 | 2 | 3 | 87 | 93 | 88 | 95 | 98 | 100 | 70 | 53 | 12 | 63 | 42 | 0 | 27 | 15 | 7 |
| | 0.375 | 7 | 3 | 7 | 55 | 68 | 37 | 97 | 90 | 80 | 62 | 55 | 3 | 48 | 37 | 7 | 27 | 10 | 5 |
| C | 3.0 | 22 | 27 | 30 | 98 | 100 | 100 | 100 | 100 | 100 | 95 | 100 | 100 | 82 | 90 | 80 | 53 | 35 | 18 |
| | 1.5 | 12 | 18 | 18 | 100 | 100 | 100 | 100 | 100 | 100 | 93 | 99 | 100 | 85 | 93 | 67 | 38 | 30 | 17 |
| | 0.75 | 2 | 2 | 2 | 100 | 100 | 100 | 100 | 100 | 100 | 70 | 82 | 77 | 68 | 58 | 18 | 33 | 18 | 8 |
| | 0.375 | 3 | 0 | 0 | 98 | 100 | 98 | 100 | 100 | 97 | 93 | 92 | 72 | 63 | 52 | 18 | 30 | 5 | 0 |

TABLE IV-continued

| | | Percent Inhibition (Herbicide Applied 0 DAT) | | | | | | | | | | | | | | | | | | |
|---|---|---|---|---|---|---|---|---|---|---|---|---|---|---|---|---|---|---|---|---|
| | | Rice WAT | | | EC WAT | | | MV WAT | | | CS WAT | | | EK WAT | | | ST WAT | | |
| Compound | Rate (Kg/Ha) | 2 | 4 | 6 | 2 | 4 | 6 | 2 | 4 | 6 | 2 | 4 | 6 | 2 | 4 | 6 | 2 | 4 | 6 |
| D | 3.0 | 8 | 7 | 5 | 99 | 100 | 100 | 100 | 98 | 98 | 67 | 65 | 60 | 85 | 75 | 22 | 22 | 28 | 18 |
| | 1.5 | 10 | 8 | 7 | 97 | 98 | 93 | 98 | 100 | 100 | 92 | 93 | 93 | 70 | 67 | 47 | 23 | 27 | 22 |
| | 0.75 | 2 | 2 | 0 | 90 | 100 | 100 | 100 | 99 | 100 | 73 | 77 | 70 | 63 | 40 | 10 | 28 | 10 | 7 |
| | 0.375 | 0 | 3 | 2 | 73 | 88 | 83 | 90 | 95 | 83 | 82 | 65 | 33 | 62 | 20 | 0 | 20 | 2 | 0 |

Reference to the data in Table IV will show that when the herbicides were applied on the day the rice was transplanted, i.e., 0 DAT, the rice was more sensitive to the compound of Example 1 ("Example 1" hereafter for brevity) and Compound C at 3 kg/ha than the other herbicides; similarly, Example 1 and Compound C exhibited higher unit activities at 0.375 kg/ha (0.34 lb/A) against the annual grasses, EC and MV; Compound C had the highest unit activity against the perennial CS, followed by Example 1 at the 4 WAT and 6 WAT observations; Example 1 exhibited the best control of both perennials, EK and ST at 2 WAT, but at 4 WAT and 6 WAT Compound C maintained the highest unit activity against EK followed by Example 1 and Compound B; at 4 WAT and 6 WAT Compounds A and C had the highest unit activity against ST.

It is to be noted that although Example 1 and Compound C generally exhibited the overall highest unit activities against the weeds in the test, the narrow margin of safety of Compound C in rice (i.e., injury rate slightly greater than 15% at 1.5 kg/ha (1.34 lb/A after 4 WAT) renders it a less suitable transplant rice herbicide than Example 1 which was safe in rice at rates above 1.5 kg/ha and slightly less than 3.0 kg/ha, under conditions of this test. Moreover, as will be shown by the data in Table V from another field test, the timing of application of the herbicide of Example 1 is much more effective when applied subsequent to the day of transplant; hence, the data shown in Table IV for the performance of Example 1 does not reflect its optimum performance.

In Table V are presented field data showing the relative performance of the compound of Example 1 and Compounds A–D applied 9 DAT, with observations being made weekly from 3 WAT to 7 WAT; again, for illustrative and representative purposes, only the early, middle and late period observations are reported in Table V, the herbicide rates and concentrations of active ingredients the same as is shown in Table IV.

TABLE V

| | | Percent Inhibition (Herbicide Applied 9 DAT) | | | | | | | | | | | | | | | | | | |
|---|---|---|---|---|---|---|---|---|---|---|---|---|---|---|---|---|---|---|---|---|
| | | Rice WAT | | | EC WAT | | | MV WAT | | | CS WAT | | | EK WAT | | | ST WAT | | |
| Cpd. | Rate (Kg/Ha) | 3 | 5 | 7 | 3 | 5 | 7 | 3 | 5 | 7 | 3 | 5 | 7 | 3 | 5 | 7 | 3 | 5 | 7 |
| Ex. 1 | 3.0 | 15 | 15 | 10 | 100 | 100 | 100 | 100 | 100 | 100 | 100 | 100 | 100 | 93 | 93 | 67 | 72 | 43 | 38 |
| | 1.5 | 10 | 7 | 5 | 100 | 98 | 100 | 100 | 100 | 100 | 82 | 100 | 67 | 82 | 65 | 0 | 40 | 13 | 7 |
| | 0.75 | 7 | 2 | 0 | 100 | 100 | 100 | 100 | 100 | 100 | 93 | 93 | 95 | 83 | 68 | 13 | 43 | 33 | 13 |
| | 0.375 | 13 | 7 | 7 | 90 | 88 | 78 | 100 | 100 | 100 | 100 | 98 | 97 | 80 | 52 | 15 | 50 | 23 | 18 |
| A | 3.0 | 12 | 7 | 5 | 93 | 93 | 90 | 100 | 100 | 100 | 88 | 100 | 100 | 68 | 40 | 0 | 52 | 23 | 13 |
| | 1.5 | 12 | 7 | 5 | 88 | 90 | 85 | 100 | 100 | 100 | 100 | 100 | 100 | 55 | 25 | 0 | 35 | 5 | 3 |
| | 0.75 | 13 | 3 | 7 | 80 | 75 | 70 | 92 | 87 | 60 | 70 | 50 | 38 | 37 | 12 | 3 | 26 | 10 | 8 |
| | 0.375 | 10 | 8 | 8 | 23 | 20 | 17 | 90 | 98 | 80 | 80 | 33 | 67 | 40 | 22 | 3 | 37 | 12 | 7 |
| B | 3.0 | 12 | 5 | 2 | 95 | 95 | 92 | 100 | 100 | 97 | 75 | 72 | 65 | 55 | 43 | 18 | 42 | 25 | 12 |
| | 1.5 | 10 | 2 | 5 | 90 | 80 | 85 | 98 | 100 | 100 | 87 | 85 | 67 | 42 | 32 | 0 | 40 | 25 | 13 |
| | 0.75 | 12 | 5 | 3 | 68 | 53 | 50 | 97 | 98 | 88 | 78 | 67 | 67 | 28 | 5 | 0 | 38 | 12 | 10 |
| | 0.375 | 12 | 0 | 5 | 57 | 55 | 47 | 100 | 95 | 77 | 93 | 100 | 77 | 27 | 3 | 0 | 5 | 2 | 5 |
| C | 3.0 | 10 | 5 | 8 | 98 | 100 | 100 | 100 | 100 | 100 | 95 | 100 | 100 | 83 | 93 | 74 | 30 | 13 | 3 |
| | 1.5 | 18 | 15 | 13 | 98 | 100 | 100 | 100 | 100 | 100 | 62 | 87 | 83 | 70 | 77 | 38 | 48 | 17 | 7 |
| | 0.75 | 10 | 7 | 8 | 92 | 95 | 97 | 100 | 100 | 100 | 93 | 93 | 82 | 75 | 68 | 32 | 32 | 8 | 0 |
| | 0.375 | 17 | 8 | 10 | 82 | 78 | 82 | 97 | 98 | 60 | 58 | 60 | 43 | 52 | 23 | 15 | 47 | 10 | 2 |
| D | 3.0 | 15 | 5 | 8 | 100 | 100 | 100 | 100 | 100 | 100 | 90 | 100 | 100 | 84 | 78 | 45 | 73 | 60 | 52 |
| | 1.5 | 10 | 5 | 7 | 78 | 75 | 78 | 100 | 100 | 100 | 77 | 77 | 100 | 52 | 30 | 0 | 43 | 25 | 22 |
| | 0.75 | 10 | 5 | 2 | 88 | 92 | 88 | 100 | 87 | 100 | 77 | 67 | 33 | 45 | 20 | 0 | 42 | 25 | 18 |
| | 0.375 | 8 | 7 | 7 | 62 | 48 | 57 | 95 | 98 | 95 | 92 | 87 | 67 | 50 | 23 | 0 | 45 | 12 | 7 |

Referring to the data in Table V, it is immediately apparent that Example 1 had the highest unit activity of all herbicides in the test against every weed in the test, except for Compound D against ST, while simultaneously maintaining safety in the rice at 3.0 kg/ha (2.67 lb/A), the maximum test rate. Similarly noteworthy is the observation that at most rates of application, particularly the lowest ones, Example 1 maintained the highest degree of selective control of EC, MV and CS for the longest period of time, i.e., 7 WAT; comparable suppression of EK as Compound C at the lowest and highest rates of application and second after Compound D in the suppression of ST at 7 WAT. It will be noted that in those instances where Compounds C and D exhibited somewhat higher unit activity than Example 1, i.e., against EK and ST, respectively at 7 WAT, both of those compounds lacked the overall degree of control and suppression of the remaining weeds in the test.

The superiority of Example 1 over the prior art herbicides is further evidenced by reference to the selectivity factors ($GR_{15}/GR_{85}$ ratios) of the respective compounds against the several weeds in the test. Thus, based on the data in Table V, Example 1 exhibited selectivity factors of 16 against EC, MV and CS in transplant rice for 3–7 WAT, whereas the selectivity factors for the prior art herbicides against the same weeds were as follows (at various periods between 3 WAT and 7 WAT): Compound A: 2, 8 and 2, respectively; Compound B: 2, 8 and 1, respectively; Compound C: 4, 8 and 4, respectively and Compound D: 1, 8 and 1, respectively. Against EK, Example 1 had a selectivity factor of about 2 up to 5 WAT; Compound C had a selectivity factor of greater than 1 at 5 WAT and Compound D had a selectivity factor of about 1 for 3 WAT and Compounds A and B were non-selective even at 3 WAT.

It is clear from the foregoing that the Compound of Example 1 exhibited overall superiority vis-a-vis the prior art compounds as a selective herbicide for transplant rice.

It is an additional advantage of the herbicides of this invention that the optimum time for application thereof to the rice is approximately nine days after transplant. Thus, the farmer can transplant his rice and let it grow for nine days while he attends to other chores needing immediate attention, or other pursuits, then return to the rice fields for application of the herbicide. In contrast, the current practice with Machete, the commercial herbicide, is to apply the herbicide within the period of three days before to four days after transplant (one practice is to apply the herbicide on the day of transplant); in this practice, the farmer is obliged to concern himself not only with transplanting the rice, but also treating with the herbicide, or vice-versa, all within a matter of hours or a few days.

In another comparative test in the greenhouse, the compound of Example 2 and Compound B were tested in Upland seeded rice. It was found that the compound of Example 2 selectively controlled Echinochloa crusgalli at 0.064 kg/ha (0.0573 lb/A) while maintaining rice safety at the maximum test rate of 1.12 kg/ha (1.0 lb/A), resulting in a selectivity factor of at least 17.5. In contrast, Compound A, (a commercial rice herbicide), required 0.14 kg/ha (0.125 lb/A) to selectively control the same weed with rice safety also maintained at 1.12 kg/ha resulting in a selectivity factor of at least 8, i.e., less than one-half of the compound of Example 2.

In further tests in the greenhouse, the compound of Example 2 was tested for its activity against annual weeds in sugarbeets at test rates within the range of 0.07 to 1.12 kg/ha (0.0625 to 1.0 lb/A). The $GR_{15}$ and $GR_{85}$ rates for sugarbeets and the various weeds are shown in Table VI; the selectivity factors for the herbicide against the weeds in sugarbeets are shown in parentheses below the weeds; "NS" means non-selective within the test limits. The following abbreviations are used in the table: barnyardgrass (BYG), wild oats (WO), downy brome (DB); redroot pigweed (RRP), blackgrass (BG), large crabgrass (LCG) and yellow foxtail (YFT).

TABLE VI

| $GR_{15}$ Rate (Kg/Ha) | $GR_{85}$ Rate (Kg/Ha) | | | | | | |
|---|---|---|---|---|---|---|---|
| Sugarbeets | BYG | WO | DB | RRP | BG | LCG | YFT |
| 0.56 | <0.07 (>8.0) | 0.28 (2.0) | 0.14 (4.0) | >1.12 (NS) | 0.21 (2.7) | 0.07 (8.0) | <0.07 (>8.0) |

The data in Table VI show that the compound of Example 2 selectively controlled every weed in the test, except redroot pigweed at rates well below 0.56 kg/ha (0.5 lb/A), thus proving the versatility of that compound as an effective herbicide in important crops.

In view of the importance of fish toxicity considerations, tests were conducted with the compound of Example 1 on carp (7 cm) according to Japanese protocol; test data are shown in Table VII. Since U.S. Pat. No. 3,955,959 mentioned above discloses carp toxicity data for butachlor (Compound A) and terbuchlor (Compound C), also obtained according to Japanese protocol, the toxicity data in said U.S. Pat. No. 3,955,959 for these compounds is also presented in Table VII for comparative purposes.

TABLE VII

| | Fish Toxicity (Carp) TLM* (PPM) | |
|---|---|---|
| Compound | 48 hours | 96 Hours |
| Ex. 1 | 3.2 | 2.4 |
| A | 1.0 | 0.76 |
| C | 1.8 | 1.4 |

*Median Tolerance Limit ($LC_{50}$)

The data in Table VII indicate that the compound of Example 1 was less than one-third as toxic to carp as Compound A, the commercial rice herbicide, and almost one-half as toxic as Compound C. Since the expected use rate of the compound of Example 1 is about one-half that of Compound A, the data in Table VII would indicate that the expected fish kill of the compound of Example 1 would be only one-sixth that of Compound A. TLM values will vary plus or minus a few tenths of a part per million from test to test within the same test protocol and from one test protocol to another, but such differences are within reproducibility limits are of no significance.

It is apparent that the above compounds may be safely used with the normal degree of care required for compounds having the indicated toxicological properties.

Therefore, it will be appreciated from the foregoing detailed description that compounds according to this invention have demonstrated unexpected and outstandingly superior herbicidal properties both absolutely and relative to structurally-relevant compounds of the prior art, one of which (Compound A) is a commercial herbicide. More particularly, the compounds of this invention have proven to be outstanding selective herbicides, particularly in the control of economically-significant Asian annual and perennial weeds in transplant rice. In more particular, compounds according to this invention exhibit outstanding control of the annual grasses Echinochloa crus-galli and *Monochoria vaginalis* and perennials such as *Cyperus serotinus, Eleocharis kurogu-wai* and *Sagittaria trifolia*, while controlling other less-resistant annual grasses and perennials, including those mentioned in Tables I, II and VI above, and others.

The herbicidal compositions of this invention, including concentrates which require dilution prior to application, contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonates.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 95 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring an aqueous mixture of a water-insoluble active ingredient and an emulsification agent until uniform and then homogenized to give a stable emulsion of very finely-divided particles. The resulting concentrated aqueous suspension is characterized by its extremely small particle size, so that when diluted and sprayed, coverage is very uniform. Suitable concentrations of these formulations contain from about 0.1-60%, preferably 5-50%, by weight of active ingredient, the upper limit being determined by the solubility limit of active ingredient in the solvent.

In another form of aqueous suspension, a water-immiscible herbicide is encapsulated to form microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total composition preferably 480 to 600 g/l. The microencapsulation process referred to here is described in more detail in the assignee's copending U.S. Ser. No. 23,566 filed Mar. 26, 1979.

Concentrates are usually solutions of active ingredient in water-immiscible or partially water-immiscible solvents, together with a surface active agent. Suitable solvents for the active ingredient of this invention include dimethylformide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles, such as preformed and screened particulate attapulgite, or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts, preferably from about 3 to 20 parts, by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Other herbicidal compounds useful in combination with the active ingredients of this invention, particularly for use in transplant rice, include, for example, methyl-5(2,4-dichlorophenoxy)-2-nitrobenzoate (common name "bifenox", active ingredient in Modown ® herbicide), 1-3-dimethyl-4-(2,4-dichlorobenzoyl)-5-pyrazolyl paratoluene sulfonate (code designation "SW-751"), α-(β-naphthoxy) propionanilide (coded MT-101"), 2,4-dichloro-3'-methoxy-4'-nitrodiphenyl ether (coded "X-52"), 3,4-dichloropropionanilide (common name "propanil"), etc. For use in other non-rice crops, other herbicidal compounds may also be combined with compounds according to this invention. For example, such other compounds include triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium
5-tert-butyl-3-(2,4-dichloro-5-isopropoxyphenyl)1,3,4-oxadiazol-2-one

Ureas

N'-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
Ethyl N,N-dipropylthiolcarbamate
S-propyl dipropylthiolcarbamate

Acetamides/Acetanilides/Anilines/Amides

2-Chloro-N,N-diallylacetamide
N,N-dimethyl-2,2-diphenylaetamide
N-(2,4-dimethyl-5-[[(trifluoromethyl)sulfonyl]amino]-phenyl)acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl) glycine and its $C_{1-6}$ monoalkyl amine and alkaline metal salts and combinations thereof

Ethers 2,4-Dichlorophenyl-4-nitrophenyl ether
2-Chloro-α,α,α-trifluoro-p-tolyl-3-ethoxy-4-nitrodiphenyl ether

Miscellaneous 2,6-Dichlorobenzonitrile
Monosodium acid methanearsonate
Disodium methanearsonate The herbicides of this invention may be used singly, as mixtures with other herbicides and may be used in sequential use with other herbicides. For example, treatments of a transplant rice crop with the herbicides of this invention may be followed with treatments of other herbicides or mixtures such as S-4-chlorobenzyl diethylthiocarbamate (common name "benthiocarb") plus 2-chloro-4,6-di(ethylamino)-1,3,5-triazine (common name "simazine") or 3-isopropyl-(1H)-benzo-2,1,3-thiadiazine-4-one-2,2-dioxide (common name "bentazone") or 4-(4-chloro-2-methylphenoxy)butyric acid (common name "MCPB"). Field tests have indicated that the compound of Example 1 is less-efficacious in direct-seeded rice, because this rice culture is less tolerant than transplant rice. However, because of the high unit activity of compounds according to this invention against annual and perennial weeds associated with rice, it is within the purview of this invention to combine these herbicides with safeners or antidotes, to enhance the tolerance of both transplanted and direct-seeded rice thereto. Exemplary safeners contemplated as useful with the herbicides of this invention include the phenylglyoxylonitrile-2-oxime cyanomethyl ether described in U.S. Pat. No. 4,152,137, 2,4-disubstituted-5-thiazolecarboxylic acids and derivatives thereof as disclosed in the assignee's copending U.S. Ser. No. 906,183 and other known safeners for 2-haloacetanilides in rice.

Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

|  | Weight Percent |
|---|---|
| I. Emulsifiable Concentrates | |
| A. Compound of Example No. 1 | 50.0 |
| Phosphate ester of ethoxylated alcohols (e.g., GAFAC ® RE-610) | 4.125 |
| Ethoxylated tertiary amines derived from fatty oils such as palm oil (e.g., Ethomeen ® C/12) | 0.875 |
| Monochlorobenzene | 13.5 |
| C9 aromatic solvent (T-400) | 31.5 |
|  | 100.00 |
| B. Compound of Example No. 2 | 46.45 |
| GAFAC RE-610 | 4.125 |
| Ethomeen ® C/12 | 0.875 |
| MCB | 48.55 |
|  | 100.00 |
| C. Compound of Example No. 1 | 5.0 |
| Calcium dodecylbenzene sulfonate/polyoxyethylene ethers blend (e.g., Atlox 3437F) | 1.0 |
| Xylene | 94.0 |
|  | 100.00 |
| II. Liquid Concentrates | |
| A. Compound of Example No.1 | 10.0 |
| Xylene | 90.0 |
|  | 100.00 |
| B. Compound of Example No. 2 | 85.0 |
| Dimethyl sulfoxide | 15.0 |
|  | 100.00 |
| C. Compound of Example No. 1 | 50.0 |
| N-methylpyrrolidone | 50.0 |
|  | 100.00 |
| D. Compound of Example No. 2 | 5.0 |
| Ethoxylated castor oil | 20.0 |
| Rhodamine B | .5 |

| | Weight Percent |
|---|---|
| Dimethyl formamide | 74.5 |
| | 100.00 |
| III. Emulsions | |
| A. Compound of Example No. 1 | 40.0 |
| Polyoxyethylene/polyoxy-propylene block copolymer with butanol (e.g., Tergitol ® XH) | 4.0 |
| Water | 56.0 |
| | 100.00 |
| B. Compound of Example No. 2 | 5.0 |
| Polyoxyethylene/polyoxy-propylene block copolymer with butanol | 3.5 |
| Water | 91.5 |
| | 100.00 |
| IV. Wettable Powders | |
| A. Compound of Example No. 1 | 25.0 |
| Sodium lignosulfonate | 3.0 |
| Sodium N-methyl-N-oleyl-taurate | 1.0 |
| Amorphous silica (synthetic) | 71.0 |
| | 100.00 |
| B. Compound of Example No. 2 | 80.0 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 1 | 10.0 |
| Sodium lignosulfonate | 3.0 |
| Sodium N-methyl-N-oleyl-taurate | 1.0 |
| Kaolinite clay | 86.0 |
| | 100.00 |
| V. Dusts | |
| A. Compound of Example No. 1 | 2.0 |
| Attapulgite | 98.0 |
| | 100.00 |
| B. Compound of Example No. 2 | 60.0 |
| Montmorillonite | 40.0 |
| | 100.00 |
| C. Compound of Example No. 1 | 30.0 |
| Bentonite | 70.0 |
| | 100.00 |
| D. Compound of Example No. 2 | 1.0 |
| Diatomaceous earth | 99.0 |
| | 100.00 |
| VI. Granules | |
| A. Compound of Example No. 1 | 15.0 |
| Granular attapulgite (20/40 mesh) | 85.0 |
| | 100.00 |
| B. Compound of Example No. 2 | 30.0 |
| Diatomaceous earth (20/40) | 70.0 |
| | 100.00 |
| C. Compound of Example No. 1 | 0.5 |
| Bentonite (20/40) | 70.0 |
| | 100.00 |
| D. Compound of Example No. 2 | 5.0 |
| Pyrophyllite (20/40) | 95.0 |
| | 100.00 |
| VII. Microcapsules | |
| A. Compound of Example No. 1 encapsulated in polyurea shell wall | 49.2 |
| Sodium lignosulfonate (e.g. Reax 88 ® B) | 0.9 |
| Water | 49.9 |
| | 100.00 |
| B. Compound of Example No. 2 encapsulated in polyurea shell wall | 10.0 |
| Potassium lignosulfonate (e.g., Reax ® C-21) | .5 |
| Water | 89.5 |
| | 100.00 |
| C. Compound of Example No. 1 encapsulated in polyurea shell wall | 80.0 |
| Magnesium salt of lignosulfate (Treax ® LTM) | 2.0 |
| Water | 18.0 |

| | Weight Percent |
|---|---|
| | 100.00 |

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. For example, in some upland-seeded rice tests, compounds according to this invention have shown a measurable amount of injury to barnyardgrass at extremely low rates. Thus, in one test, the compound or Example 2 exhibited 20% control of barnyardgrass at 0.0087 kg/ha (0.0078 lb/A). One skilled in the art can readily determine from this specification, including the above example, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

What is claimed is:

1. Compounds having the formula

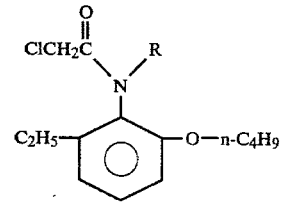

wherein R is a $C_{1-4}$ alkyl radical.

2. Compound according to claim 1 which is N-methyl-2'-n-butoxy-6'-ethyl-2-chloroacetanilide.

3. Compound according to claim 1 which is N-ethyl-2'-n-butoxy-6'-ethyl-2-chloroacetanilide.

4. Herbicidal compositions comprising an adjuvant and a herbicidally effective amount of a compound of the formula

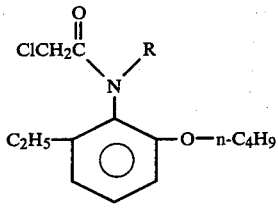

wherein R is a $C_{1-4}$ alkyl radical.

5. Composition according to claim 4 wherein said compound is N-methyl-2'-n-butoxy-6'-ethyl-2-chloroacetanilide.

6. Composition according to claim 4 wherein said compound is N-ethyl-2'-n-butoxy-6'-ethyl-2-chloroacetanilide.

7. Method for combatting undesirable plants in crops which comprises applying to the locus of said plants a herbicidally effective amount of a compound of the formula

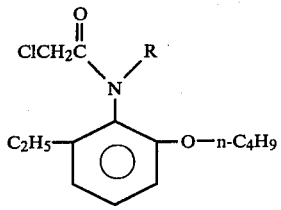

wherein R is a $C_{1-4}$ alkyl radical.

8. Method according to claim 7 wherein said crop is transplanted rice.

9. Method according to claim 8 wherein said compound is N-methyl-2'-n-butoxy-6'-ethyl-2-chloroacetanilide.

10. Method according to claim 8 wherein said compound is N-ethyl-2'-n-butoxy-6'-ethyl-2-chloroacetanilide.

11. Method for combatting weeds in transplant rice which comprises applying to the locus thereof a herbicidally effective amount of N-methyl-2'-n-butoxy-6'-ethyl-2-chloroacetanilide.

12. Method for combatting weeds in transplant rice which comprises applying to the locus thereof a herbicidally effective amount of N-ethyl-2'-n-butoxy-6'-ethyl-2-chloroacetanilide.

* * * * *